(12) United States Patent
Sugegaya et al.

(10) Patent No.: US 12,423,805 B2
(45) Date of Patent: Sep. 23, 2025

(54) IMAGE DISPLAY APPARATUS, NON-TRANSITORY COMPUTER READABLE STORAGE MEDIUM STORING CONTROL PROGRAM, AND IMAGE DISPLAY SYSTEM

(71) Applicant: Konica Minolta, Inc., Tokyo (JP)

(72) Inventors: Naotoshi Sugegaya, Hino (JP); Kenta Shimamura, Hino (JP); Noritsugu Matsutani, Musashino (JP)

(73) Assignee: Konica Minolta, Inc., Tokyo (JP)

( * ) Notice: Subject to any disclaimer, the term of this patent is extended or adjusted under 35 U.S.C. 154(b) by 371 days.

(21) Appl. No.: 17/694,955

(22) Filed: Mar. 15, 2022

(65) Prior Publication Data

US 2022/0309658 A1    Sep. 29, 2022

(30) Foreign Application Priority Data

Mar. 25, 2021   (JP) ................. 2021-052369

(51) Int. Cl.
| | | |
|---|---|---|
| *G06T 11/00* | (2006.01) | |
| *G06T 7/00* | (2017.01) | |
| *G06T 7/20* | (2017.01) | |
| *A61B 90/00* | (2016.01) | |

(52) U.S. Cl.
CPC .............. *G06T 7/0012* (2013.01); *G06T 7/20* (2013.01); *G06T 11/00* (2013.01); *A61B 90/37* (2016.02); *A61B 2090/374* (2016.02); *G06T 2207/10081* (2013.01); *G06T 2207/10088* (2013.01); *G06T 2207/10132* (2013.01)

(58) Field of Classification Search
CPC ......... G06T 7/0012; G06T 7/20; G06T 11/00; G06T 2207/10081; G06T 2207/10088; G06T 2207/10132; G06T 2207/30061; G06T 7/215; G06T 7/269; G06T 11/008; A61B 90/37; A61B 2090/374; G16H 20/40; G16H 50/20; G16H 30/20; G16H 30/40; G16H 40/67

See application file for complete search history.

(56) References Cited

U.S. PATENT DOCUMENTS

| | | | |
|---|---|---|---|
| 2018/0276816 A1* | 9/2018 | Kaneko | A61B 6/507 |
| 2018/0360325 A1* | 12/2018 | Robinson | A61B 5/02427 |
| 2019/0107989 A1* | 4/2019 | Mizobe | G16H 40/63 |

(Continued)

FOREIGN PATENT DOCUMENTS

| | | |
|---|---|---|
| JP | 2004305486 A | 11/2004 |
| JP | 2006255217 A | 9/2006 |

(Continued)

OTHER PUBLICATIONS

Office Action issued in Japanese Application No. 2021-052369; Dated Oct. 3, 2023 (6 pages).

(Continued)

*Primary Examiner* — Md K Talukder
(74) *Attorney, Agent, or Firm* — Osha Bergman Watanabe & Burton LLP

(57) ABSTRACT

An image display apparatus includes: a hardware processor that obtains frame images showing a dynamic state of a subject; and a display that displays accessory information indicating a movement decrease region with respect to the obtained frame images, the accessory information being superimposed on consecutive frame images of the frame images.

16 Claims, 8 Drawing Sheets

(56) References Cited

U.S. PATENT DOCUMENTS

| | | | |
|---|---|---|---|
| 2019/0295247 A1* | 9/2019 | Miyajima | A61B 6/12 |
| 2020/0160514 A1* | 5/2020 | Katsuhara | G06T 7/0012 |
| 2020/0379636 A1* | 12/2020 | Takasawa | G11B 27/28 |
| 2021/0125333 A1* | 4/2021 | Oliveira Ferreira | G06T 11/003 |
| 2022/0309658 A1* | 9/2022 | Sugegaya | G06T 7/20 |

FOREIGN PATENT DOCUMENTS

| | | |
|---|---|---|
| JP | 2015136566 A | 7/2015 |
| JP | 2019-180899 A | 10/2019 |

OTHER PUBLICATIONS

Office Action issued in corresponding Japanese Patent Application No. 2021-052369, dated Dec. 19, 2023 (6 pages).

* cited by examiner

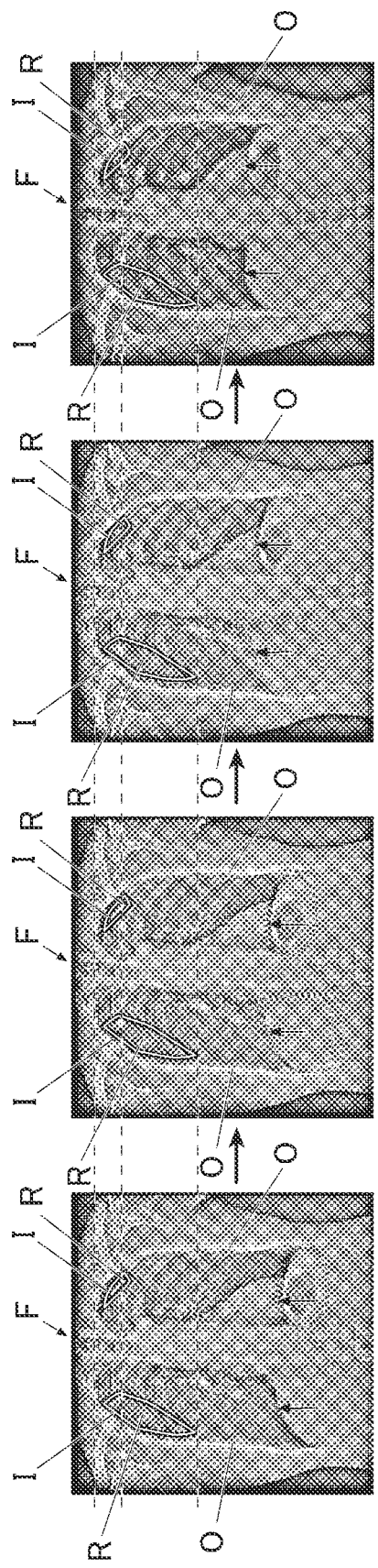

IMAGE DISPLAY APPARATUS, NON-TRANSITORY COMPUTER READABLE STORAGE MEDIUM STORING CONTROL PROGRAM, AND IMAGE DISPLAY SYSTEM

CROSS-REFERENCE TO RELATED APPLICATIONS

The entire disclosure of Japanese Patent Application No. 2021-052369 filed on Mar. 25, 2021 is incorporated herein by reference.

BACKGROUND

Technical Field

The present disclosure relates to an image display apparatus, a non-transitory computer readable storage medium storing a control program, and an image display system.

Description of Related Art

If presence or absence of pleural adhesion can be determined before a surgical operation on lung fields is performed, the surgical time can be estimated with a high degree of accuracy by the time required for adhesiolysis or the like being taken into account.

As disclosed, for example, in JP 2015-136566 A, there has been proposed a technology of extracting displacement of the diaphragm from a dynamic image and determining whether the phase of the displacement of the diaphragm and the phase of respiration match. In JP 2015-136566 A, there is disclosed that one of the causes for the phase of the displacement of the diaphragm and the phase of the respiration not to match is presence of adhesion.

That is, there has been known a technology to suggest presence of a disease, such as adhesion, on the basis of a dynamic image.

In the existing circumstances, a doctor who interprets a dynamic image makes the final judgement about whether a disease, such as adhesion, is present and/or about the position of a disease.

Hence, dynamic images, which are interpreted by doctors, may be a dynamic image that allows doctors to easily recognize, with their eyes, where a disease is captured in the dynamic image.

However, if a dynamic image is reproduced in a state in which accessory information, such as a mark, is attached to some of frame images of the dynamic image, the accessory information flickers during the reproduction of the dynamic image.

To deal with this issue, accessory information may be attached to all consecutive frame images of a dynamic image.

However, if accessory information attached to one frame image of a dynamic image is attached to consecutive frame images of the dynamic image, and the dynamic image is reproduced, the accessory information slips out of place during the reproduction because the accessory information that is still is attached to the dynamic image that is a moving image.

SUMMARY

One or more embodiments of the present disclosure improve visibility in interpreting a plurality of frame images.

According to a first aspect of the present disclosure, there is provided an image display apparatus including:
a hardware processor that obtains a plurality of frame images showing a dynamic state of a subject; and
a display that displays accessory information indicating a movement decrease region in the obtained plurality of frame images, the accessory information being superimposed on consecutive frame images of the plurality of frame images.

According to a second aspect of the present disclosure, there is provided an image display apparatus including a display that displays an image in which accessory information indicating a movement decrease region in a plurality of frame images showing a dynamic state of a subject is superimposed on consecutive frame images of the plurality of frame images.

According to a third aspect of the present disclosure, there is provided a non-transitory computer readable storage medium storing a control program to cause an image display apparatus including a hardware processor and a display to:
obtain a plurality of frame images showing a dynamic state of a subject; and
display accessory information indicating a movement decrease region in the obtained plurality of frame images, the accessory information being superimposed on consecutive frame images of the plurality of frame images.

According to a fourth aspect of the present disclosure, there is provided an image display system including:
an image display apparatus;
a hardware processor that obtains a plurality of frame images showing a dynamic state of a subject; and
a display that displays accessory information indicating a movement decrease region in the obtained plurality of frame images, the accessory information being superimposed on consecutive frame images of the plurality of frame images.

BRIEF DESCRIPTION OF THE DRAWINGS

The advantages and features provided by one or more embodiments of the present disclosure will become more fully understood from the detailed description given hereinbelow and the appended drawings that are given by way of illustration only, and thus are not intended as a definition of the limits of the present disclosure, wherein:

FIG. 10 shows an example of frame images displayed by the image display apparatus included in the image display system according to one or more embodiments;

DETAILED DESCRIPTION OF EMBODIMENTS

Hereinafter, embodiments of the present disclosure will be described with reference to the drawings. However, the scope of the present disclosure is not limited to the embodiments or illustrated examples.

1. Outline of Image Display System

First, an outline of an image display system (hereinafter "system 100") of one or more embodiments will be described.

Figure 1:
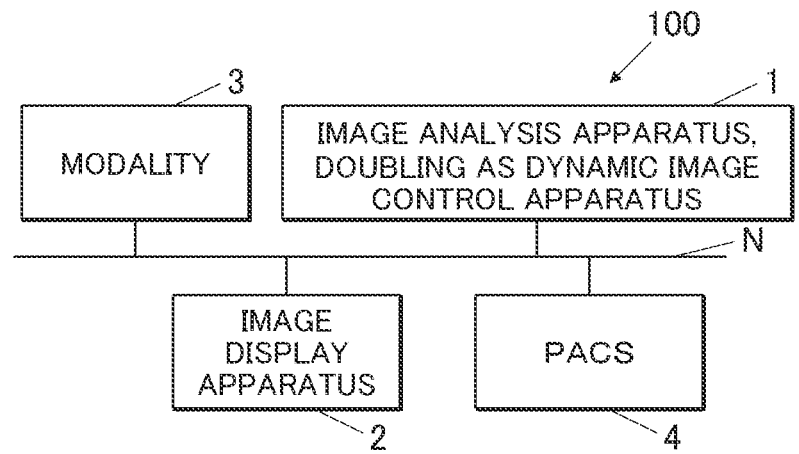
FIG. 1 is a block diagram showing an example of an image display system according to one or more embodiments of the present disclosure.

FIG. 1 is a block diagram of the system 100.

[1-1. Schematic Configuration of Image Display System]

As shown in FIG. 1, the system 100 includes an image analysis apparatus 1 and an image display apparatus 2.

The system 100 according to one or more embodiments further includes a modality 3 and a picture archiving and communication system (hereinafter "PACS 4").

The apparatuses 1 to 4 can communicate with one another, for example, via a communication network N (local area network (LAN), wide area network (WAN), Internet, etc.).

The system 100 may be able to communicate with a not-shown hospital information system (HIS), a not-shown radiology information system (RIS) and/or the like.

[Modality]

The modality 3 is an imaging apparatus that images a target site of a subject to generate digital data (hereinafter "image data") of medical images where the target site is captured.

Examples of the modality 3 include a flat panel detector (FPD) apparatus, a computed tomography (CT) apparatus, a magnetic resonance imaging (MRT) apparatus and an ultrasound diagnostic apparatus.

The modality 3 according to one or more embodiments can generate, in addition to still images, a plurality of frame images F showing the dynamic state of the subject.

The "(plurality of) frame images F showing the dynamic state of the subject" refer to a plurality of medical images obtained by continuously radiographing one target site doing a certain movement/motion along the time axis.

The "(plurality of) frame images F showing the dynamic state of the subject" are, for example, a dynamic image.

The modality 3 according to one or more embodiments may include a not-shown console for setting various imaging conditions and for controlling operation of each component of the modality 3.

The modality 3 may be installed in an imaging room, or may be configured to move.

[Image Analysis Apparatus]

The image analysis apparatus 1 is configured by a PC, a dedicated apparatus or the like The image analysis apparatus 1 analyzes a plurality of frame images F generated by the modality 3.

The image analysis apparatus 1 according to one or more embodiments doubles as a dynamic image control apparatus.

Details of the image analysis apparatus 1 will be described later.

[Picture Archiving and Communication System]

The PACS 4 is configured by a PC, a dedicated apparatus or the like.

The PACS 4 stores image data generated by the modality 3, image data processed by the image analysis apparatus 1 and so forth.

The PACS 4 according to one or more embodiments stores multiple image data by accumulating these in a database.

[Image Display Apparatus]

The image display apparatus 2 displays medical images based on image data obtained from the image analysis apparatus 1, the modality 3 or the PACS 4.

[1-2. Flow of Diagnosis Using Image Display System]

A diagnose(s) using thus-configured system 100 according to one or more embodiments is made as follows.

First, a user (technician, etc.) photographs the target site of an examinee by using the modality 3, so that the modality 3 generates image data of medical image(s) (a plurality of frame images F or a still image(s)) where the target site is captured.

When the modality 3 generates the image data, the modality 3 sends the image data to the image analysis apparatus 1, the image display apparatus 2 or the PACS 4.

When the image analysis apparatus 1 obtains image data, the image analysis apparatus 1 analyzes a plurality of frame images F based on the image data.

When, like one or more embodiments, the image data is image data of a plurality of frame images F, the image analysis apparatus 1 performs a dynamic image control process, which will be described later, and sends the image data on which the dynamic image control process has been performed to the image display apparatus 2 or the PACS 4.

When the image display apparatus 2 obtains image data from the image analysis apparatus 1, the modality 3 or the PACS 4, the image display apparatus 2 displays medical images based on the obtained image data.

A doctor(s) makes a diagnosis for the examinee on the basis of the medical images displayed by (on) the image display apparatus 2.

When the PACS 4 obtains image data, the PACS 4 accumulates the obtained image data in a database.

[1-3. Modifications of Image Display System]

So far, the system 100 in which the image analysis apparatus 1 doubles as a dynamic image control apparatus has been described, but another apparatus may double as a dynamic image control apparatus.

Figure 2:
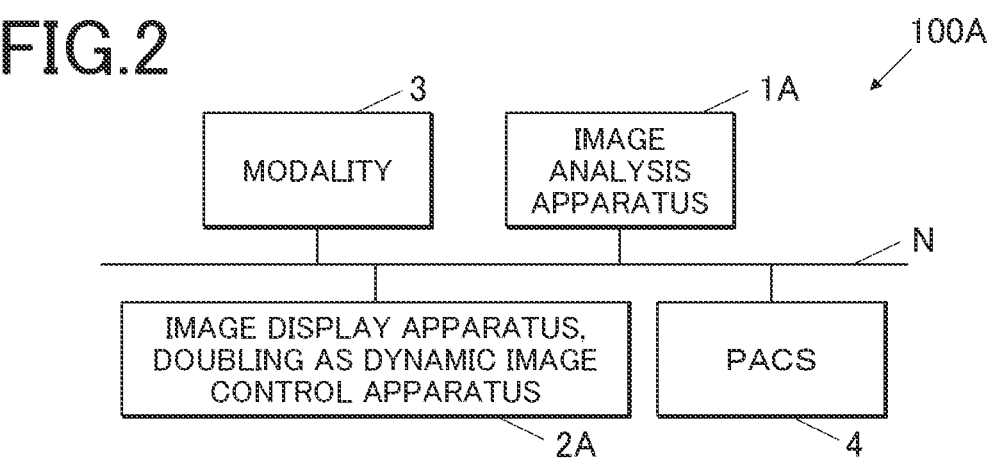
FIG. 2 is a block diagram showing another example of the image display system according to one or more embodiments.

More specifically, for example, as shown in FIG. 2, a system 100A may be configured, the system 100A including, in addition to the above-described modality 3 and PACS 4, an image analysis apparatus 1A that does not have a function as a dynamic image control apparatus and an image display apparatus 2A that doubles as a dynamic image control apparatus.

Figure 3:
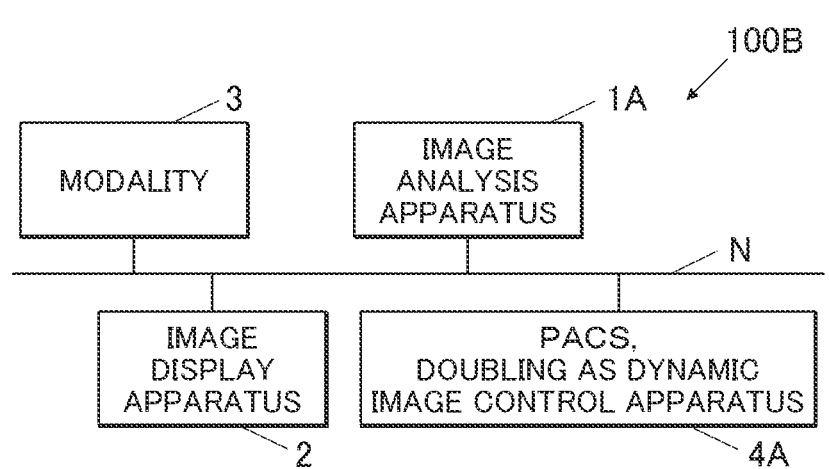
FIG. 3 is a block diagram showing another example of the image display system according to one or more embodiments.

Alternatively, for example, as shown in FIG. 3, a system 100B may be configured, the system 100B including, in addition to the above-described image display apparatus 2 and modality 3, an image analysis apparatus 1A that does not have a function as a dynamic image control apparatus and a PACS 4A that doubles as a dynamic image control apparatus.

So far, the system 100 in which the image analysis apparatus 1 and the image display apparatus 2 are separate apparatuses has been described, but the image analysis apparatus 1 and the image display apparatus 2 may be integrated.

Figure 4:
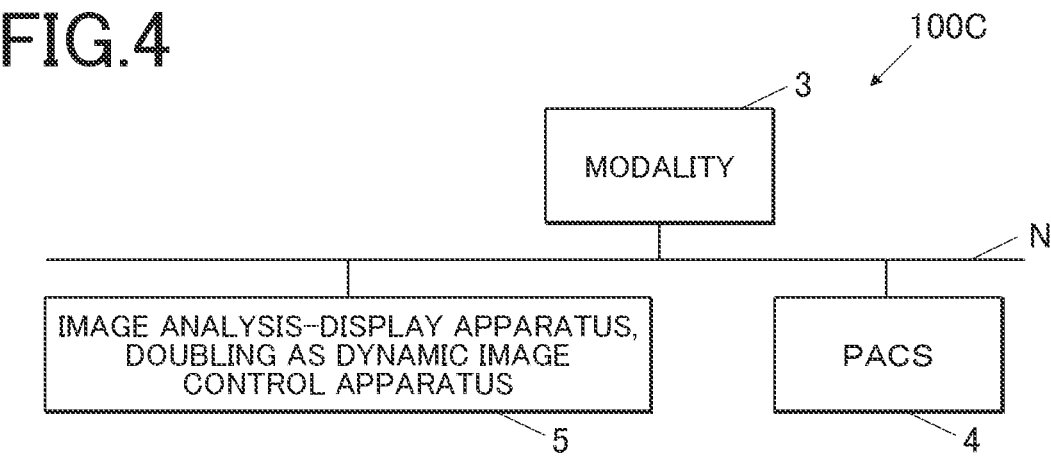
FIG. 4 is a block diagram showing another example of the image display system according to one or more embodiments.

More specifically, for example, as shown in FIG. 4, a system 100C may be configured, the system 100C including, in addition to the above-described modality 3 and PACS 4, an image analysis-display apparatus 5 that has functions as an image analysis apparatus 1 and an image display apparatus 2 and also serves as a dynamic image control apparatus.

So far, the system 100 in which one of the apparatuses doubles as a dynamic image control apparatus has been described, but an independent dynamic image control apparatus may be provided.

Figure 5:
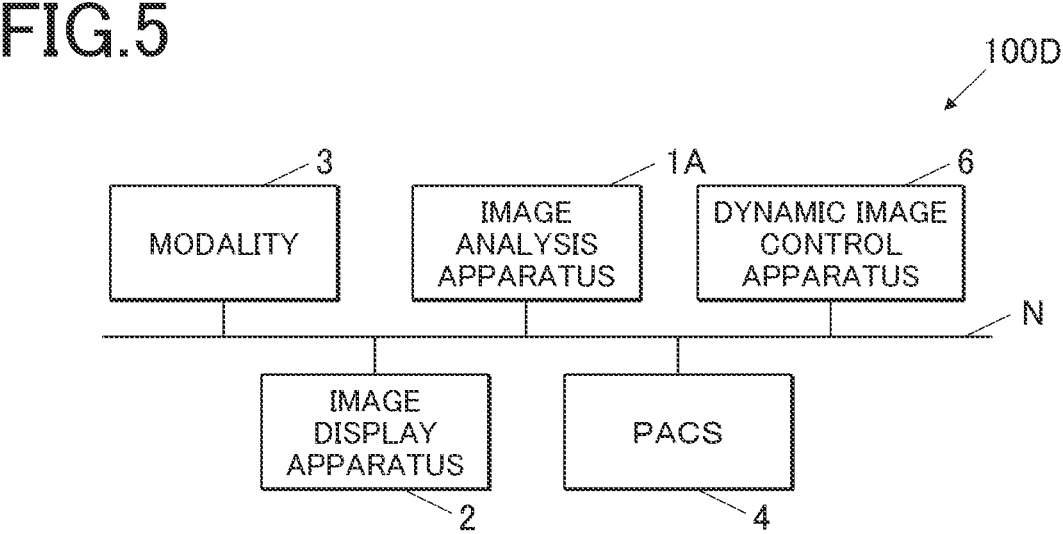
FIG. 5 is a block diagram showing another example of the image display system according to one or more embodiments.

More specifically, for example, as shown in FIG. 5, a system 100D may be configured, the system 100D including, in addition to the above-described image display apparatus 2, modality 3 and PACS 4, an image analysis apparatus 1A that does not have a function as a dynamic image control apparatus, and a dynamic image control apparatus 6.

2. Details of Image Analysis Apparatus

Next, details of the image analysis apparatus 1 (which doubles as a dynamic image control apparatus) included in the above-described system 100 will be described.

Figure 6:
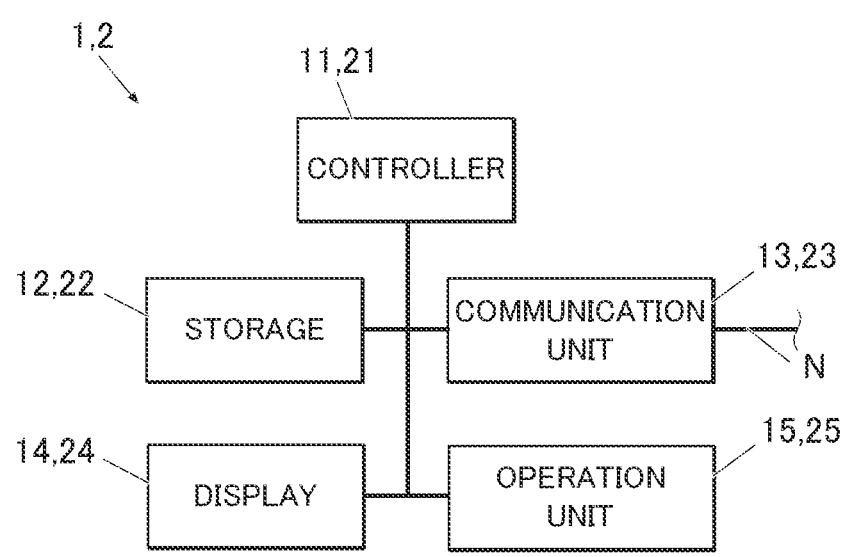
FIG. 6 is a block diagram of an image analysis apparatus (and an image display apparatus) included in the image display system according to one or more embodiments.
Figure 7:
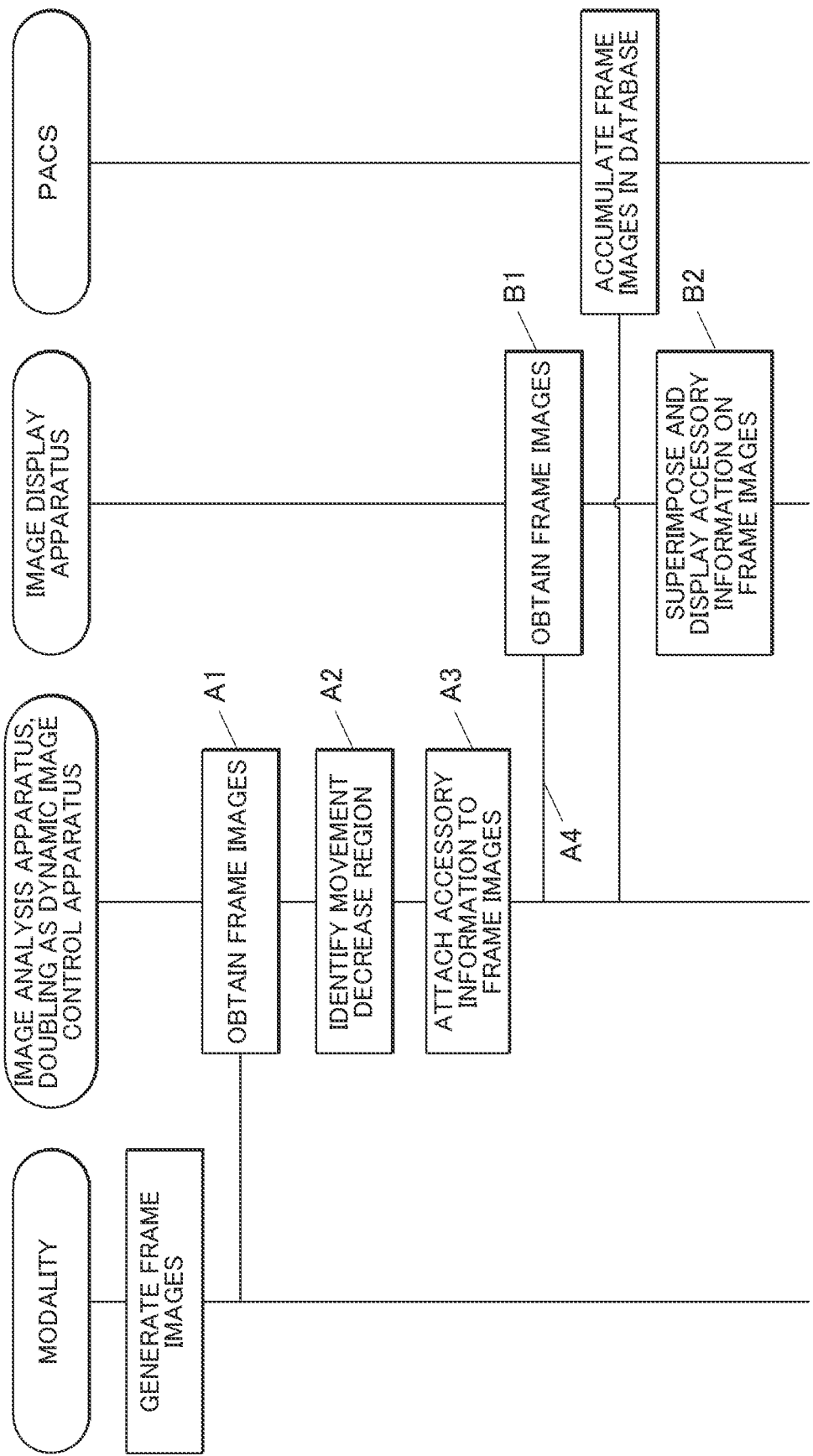
FIG. 7 is a sequence diagram showing an example of operation of the image display system according to one or more embodiments.
Figure 8A:
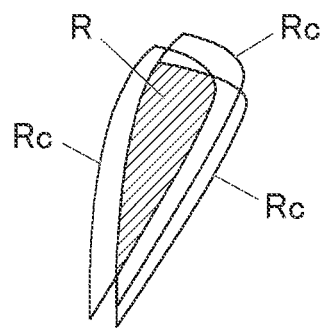
FIG. 8A is a conceptual diagram showing an example of how the image analysis apparatus included in the image display system according to one or more embodiments identifies a movement decrease region.
Figure 8B:
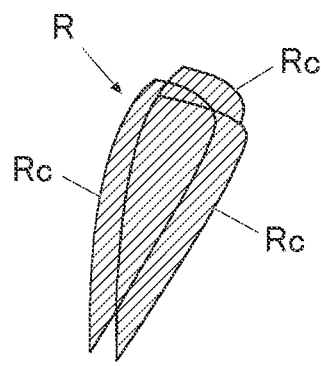
FIG. 8B is a conceptual diagram showing another example of how the image analysis apparatus included in the image display system according to one or more embodiments identifies the movement decrease region.
Figure 8C:
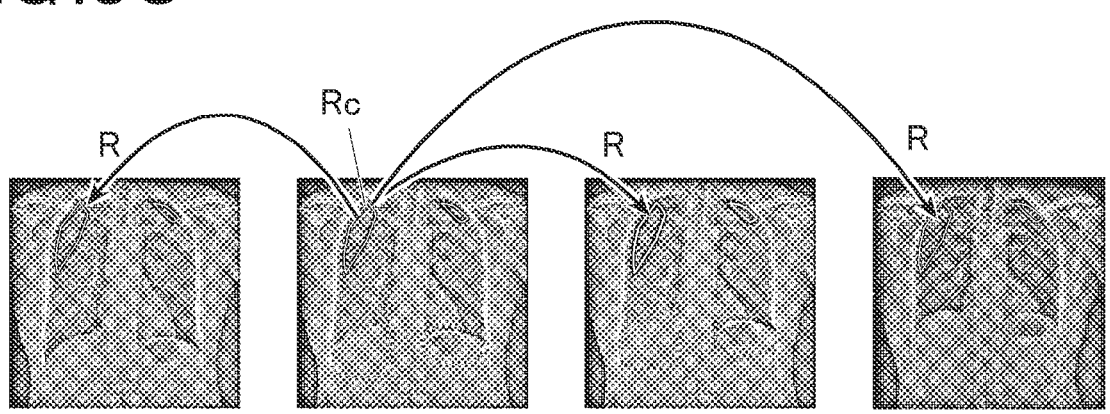
FIG. 8C is a conceptual diagram showing another example of how the image analysis apparatus included in the image display system according to one or more embodiments identifies the movement decrease region.

FIG. 6 is a block diagram of the image analysis apparatus 1. FIG. 7 is a sequence diagram showing operation of the system 100. FIG. 8A, FIG. 8B and FIG. 8C are conceptual diagrams showing examples of how the image analysis apparatus 1 identifies a movement decrease region.

The reference signs after commas in FIG. 6 are for the image display apparatus 2, which will be described later.

[2-1. Configuration of Image Analysis Apparatus]

As shown in FIG. 6, the image analysis apparatus 1 includes a first controller 11 (hardware processor), a first storage 12, a first communication unit 13, a first display 14 and a first operation unit 15.

These components 11 to 15 are electrically connected to one another by a bus or the like.

The first controller 11 includes a CPU (Central Processing Unit) and a RAM (Random Access Memory).

The CPU of the first controller 11 reads various programs stored in the first storage 12, loads them to the RAM, performs various processes in accordance with the loaded programs, and performs centralized control of operation of the components of the image analysis apparatus 1.

The first storage 12 is configured by a nonvolatile memory, a hard disk and/or the like.

The first storage 12 stores the various programs, which are performed by the first controller 11, parameters necessary for execution of the programs, and so forth.

The first storage 12 may be able to store image data of medical images.

The first communication unit 13 is configured by a communication module or the like.

The first communication unit 13 sends and receives various signals and various data to and from other apparatuses (image display apparatus 2, modality 3, PACS 4, etc.) connected thereto via the communication network N with wires or wirelessly.

The first display 14 is configured by a liquid crystal display (LCD), a cathode ray tube (CRT) or the like.

The first display 14 displays medical images or the like in accordance with image signals received from the first controller 11.

The first operation unit 15 is configured by a keyboard (cursor keys, numeric input keys, various function keys, etc.), a pointing device (a mouse, etc.), a touchscreen overlaid on the surface of the first display 14, and/or the like.

The first operation unit 15 outputs, to the first controller 11, control signals corresponding to operations made by a user.

The image analysis apparatus 1 may not include the first display 14 and the first operation unit 15, and may receive control signals from a dedicated input apparatus provided separately from the image analysis apparatus 1 and output image signals to a dedicated monitor provided separately from the image analysis apparatus 1 via the first communication unit 13 or the like, for example.

If another apparatus(es) (image display apparatus 2, PACS 4, etc.) includes a display and an operation unit, the image analysis apparatus 1 may receive control signals from the operation unit of another apparatus and output image signals to the display of the/another apparatus (or may share a display and an operation unit with another apparatus(es)).

[2-2. Operation of Image Analysis Apparatus]

The first controller 11 of the image analysis apparatus 1 configured as described above performs the abovementioned dynamic image control process based on a control program stored in the first storage 12, when a predetermined condition is met.

Examples of the predetermined condition include a condition that power of the image analysis apparatus 1 is turned on, a condition that image data is obtained from another apparatus, a condition that a predetermined control signal is received from another apparatus, and a condition that a predetermined operation is made on the first operation unit 15.

The dynamic image control process includes, as shown in FIG. 7, an image obtainment step (Step A1), a region identification step (Step A2), an attachment control step (Step A3) and an output step (Step A4).

[2-2-1. Image Obtainment Step]

In the dynamic image control process, the first controller 11 first performs the image obtainment step (Step A1).

In this image obtainment step, the first controller 11 obtains a plurality of frame images F.

In the image obtainment step of one or more embodiments, the first controller 11 receives image data of a plurality of frame images F via the first communication unit 13.

If the image analysis apparatus 1 includes a reader for a storage medium, the first controller 11 may read the image data from a storage medium with the reader.

If the first controller 11 starts the dynamic image control process by obtaining a plurality of frame images F as a trigger, this image obtainment step is unneeded.

[2-2-2. Region Identification Step]

After obtaining the plurality of frame images F, the first controller 11 performs the region identification step (Step A2).

In this region identification step, the first controller 11 identifies a movement decrease region(s) of a predetermined structure(s) O (hereinafter "decrease region R") from the obtained frame images F.

The "structure" is not particularly limited as far as it is a structure of the subject. Examples of the structure include organs and tissues of the subject. Examples of the organs and tissues include lungs, heart, stomach and joints.

The "decrease region R" is a region where a disease, such as pleural adhesion, is suspected, and a region that hardly moves while a plurality of frame images F is being reproduced although it is supposed to move.

In this region identification step, the first controller 11 identifies the decrease region R automatically or under manual operation.

Examples of a method for identifying the decrease region R in one or more embodiments of the present disclosure include: extracting, from the beginning, parameters such as coordinates common to all frames (frame images F) as the decrease region R; and extracting coordinates corresponding to each frame, and then extracting coordinates common to all frames from these as the decrease region R.

The coordinate values may be extracted in accordance with a relative positional relationship between frames or structures.

After feature points are extracted in such a manner, the display area(s) for accessory information is identified (or specified).

In the case of automatic identification, the first controller 11 identifies the decrease region R by detection from frame images F.

More specifically, for example, about frame images F of an analysis target section, the first controller 11 performs optical flow between frame images F adjacent in the time direction (hereinafter "between adjacent frame images") to, for each predetermined small region in the frame images F, obtain corresponding points between every adjacent frame images F and calculate a movement vector.

Next, for each small region, the first controller 11 merges (combines) the movement vectors to calculate a movement vector indicating a movement from the start frame image to the end frame image of the analysis target frame images.

Then, for each small region, the first controller 11 calculates a movement amount in the body axis direction (upward) (length of the movement vector in the body axis direction (upward)) on the basis of the calculated movement vector.

If the calculated length of the movement vector in the body axis direction (movement amount of a predetermined structure) is not greater than (or is less than) a predetermined threshold value, the first controller 11 determines that adhesion is present in the small region, whereas if the calculated length is greater than (or is not less than) the threshold value, the first controller 11 determines that no adhesion is present in the small region.

The threshold value (if it is a fixed value) for determining presence or absence of adhesion is preferably 6 mm and further preferably 1.5 mm, for example.

The threshold value is not limited to the above values bur may be another value, such as 0.5 mm.

The first controller 11 may determine presence or absence of adhesion by using any of the following indicators.

The movement amount of the structure O is not greater than (or is less than) a predetermined value % of the movement amount thereof of healthy people (reference value).

The movement amount of the structure O is not greater than (or is less than) a predetermined value mm (or a predetermined value pixel(s)).

Variation of a signal value(s) of a pixel(s) of a region where the structure O is shown is not greater than (or is less than) a predetermined value.

The movement amount of the structure O is not greater than (or is less than) a predetermined value % of the movement amount of its surrounding region.

Then, the first controller 11 treats a small region or a group of small regions determined as the region(s) where adhesion is present, as a candidate region Rc for the decrease region R, and identifies the decrease region R from the candidate region(s) Rc by using any of the following methods.

Identify, about each frame image F, a candidate region Rc for the decrease region R, and for example, as shown in FIG. 8A, identify a region common to (an overlapping region of) the candidate regions Rc of the respective frame images F as the decrease region R.

Identify, about each frame image F, a candidate region Rc for the decrease region R, and for example, as shown in FIG. 8B, identify the largest region (including overlapping region(s) and no-overlapping region(s)) formed by the candidate regions Rc of the respective frame images F as the decrease region R.

Identify, about a certain frame image F (a frame image F where the lung fields at the maximal inspiratory level is captured, a frame image F where the lung fields at the maximal expiratory level is captured, etc.), a candidate region Rc for the decrease region R, and identify the candidate region Rc as the decrease region R common to the frame images F.

In this manner, in respective frame images F, decrease regions R having the same shape are identified at the same position (coordinates).

On the other hand, in the case of manual identification, the first controller 11 identifies the decrease region R by user input.

More specifically, the first controller 11 causes the first display 14 to display the frame images F obtained in the image obtainment step, and also puts the first operation unit 15 in a state of being capable of receiving a region setting operation(s) from the user.

When the user makes a predetermined region setting operation to a region(s) in the (respective) frame images F displayed by the first display 14, the first controller 11 identifies the region as the decrease region R. Examples of the region setting operation include tracing the contours of a region with a cursor, clicking repeatedly while moving the cursor along the contours of a region, tracing the contours of a region with a finger, and touching multiple points on the contours of a region.

In this region identification step, the first controller 11 may identify the decrease region R semi-automatically.

More specifically, when the user makes a predetermined area setting operation to an area(s) in the (respective) frame images F displayed by the first display 14, the first controller 11 may automatically identify the decrease region R in the set area.

Alternatively, after the first controller 11 automatically identifies the decrease region R, the first controller 11 may fine-adjust the area of the decrease region R by user input.

In the region identification step (automatic), the first controller 11 may generate one composite image (summary image) from the frame images F.

In the region identification step (manual), the first controller 11 may cause the display of another apparatus (image display apparatus 2 or PACS 4) to display the frame images F, and receive a region setting operation made on the operation unit of the/another apparatus.

[2-2-3. Attachment Control Step]

After identifying the decrease region R, the first controller 11 performs the attachment control step (Step A3).

In this attachment control step, the first controller 11 performs control to attach accessory information I indicating the identified decrease region R to frame images F.

Examples of the accessory information I include a frame-shaped mark superimposed on the decrease region R, an arrow-shaped mark pointing to the decrease region R, text information, a symbol, a figure, an image, a sound, and any combinations of these.

Examples of a method for attaching (superimposing) the accessory information I include: overlaying the accessory information I on an image; and embedding the accessory information I in an image.

A region where the accessory information I is attached (indicated or shown) is not particularly limited as far as it is a region on a screen, such as a region to which attention is likely to be paid.

In the attachment control step of one or more embodiments, the first controller 11 first generates one (piece of) accessory information I from information of the identified decrease region R (region having a movement amount being not greater than or being less than a threshold value).

More specifically, the first controller 11 generates, for example, a frame-shaped mark that is the same as the contour line of the decrease region R in shape.

In this attachment control step, the first controller 11 may generate a mark that is the same as the decrease region R in shape and filled (solid-colored) or a mark with which the surroundings of the decrease region R are filled. The mark with which the surroundings of the decrease region R are filled lets doctors easily notice the decrease region R.

The first controller 11 then attaches (indicates or shows) the generated one accessory information I to (at) the same position (coordinates) in respective frame images F.

This "(plurality of) frame images F" refers to the number of frame images F within the range of 90% to 100% of all the frame images F.

This "plurality" is preferably 100% (all).

Even if this "plurality" is below 100%, the "(plurality of) frame images F" may be consecutive frame images F.

If, in addition to a plurality of frame images F, a plurality of analyzed frame images obtained by analyzing the plurality of frame images F, a plurality of processed frame images obtained by processing the plurality of frame images F and/or the like are present, in this attachment control step, the first controller 11 may attach the accessory information I to each frame image group (instance) or a set (series) of multiple types of frame image groups.

In this attachment control step, the first controller 11 may attach (indicate or show) the accessory information I to (within or in the vicinity of) the decrease region R of the composite image generated from frame images F.

The "composite image" is one still image generated on the basis of frame images F (e.g., the summary image generated in the region identification step).

[2-2-4. Output Step]

After attaching the accessory information I to the frame images F, the first controller 11 performs the output step (Step A4).

In this output step, the first controller 11 outputs the frame images F with the accessory information I attached to the image display apparatus 2 or the PACS 4.

In the output step of one or more embodiments, the first controller 11 sends image data of the frame images F to another apparatus via the first communication unit 13.

<Details of Image Display Apparatus>

Next, details of the image display apparatus 2 included in the above-described system 100 will be described.

FIG. 9A, FIG. 9B, FIG. 9C and FIG. 10 show examples of frame images that are displayed by the image display apparatus 2.

[3-1. Configuration of Image Display Apparatus]

As shown in FIG. 6, the image display apparatus 2 includes a second controller 21 (hardware processor), a second storage 22, a second communication unit 23, a second display 24 (display) and a second operation unit 25.

These components 21 to 25 are electrically connected to one another by a bus or the like.

The second controller 21 includes a CPU and a RAM.

The CPU of the second controller 21 reads various programs stored in the second storage 22, loads them to the RAM, performs various processes in accordance with the loaded programs, and performs centralized control of operation of the components of the image display apparatus 2.

The second storage 22 is configured by a nonvolatile memory, a hard disk and/or the like.

The second storage 22 stores the various programs, which are performed by the second controller 21, parameters necessary for execution of the programs, and so forth.

The second storage 22 may be able to store image data of medical images.

The second communication unit 23 is configured by a communication module or the like.

The second communication unit 23 sends and receives various signals and various data to and from other apparatuses (image analysis apparatus 1, modality 3, PACS 4, etc.) connected thereto via the communication network N with wires or wirelessly.

The second display 24 is configured by an LCD, a CRT or the like.

The second display 24 displays medical images or the like in accordance with image signals received from the second controller 21.

The second operation unit 25 is configured by a keyboard (cursor keys, numeric input keys, various function keys, etc.), a pointing device (a mouse, etc.), a touchscreen overlaid on the surface of the second display 24, and/or the like.

The second operation unit 25 outputs, to the second controller 11, control signals corresponding to operations made by a user.

The image display apparatus 2 may not include the second display 24 and the second operation unit 25, and may receive control signals from a dedicated input apparatus provided separately from the image display apparatus 2 and output image signals to a dedicated monitor provided separately from the image display apparatus 2 via the second communication unit 23 or the like, for example.

If another apparatus(es) (image analysis apparatus 1, PACS 4, etc.) includes a display and an operation unit, the image display apparatus 2 may receive control signals from the operation unit of another apparatus and output image signals to the display of the/another apparatus (or may share a display and an operation unit with another apparatus(es)).

[3-2. Operation of Image Display Apparatus]

The second controller 21 of the image display apparatus 2 configured as described above operates as follows.

For example, the second controller 21 performs an image display process based on a control program stored in the second storage 22, when a predetermined condition is met.

Examples of the predetermined condition include a condition that power of the image display apparatus 2 is turned on, a condition that image data is obtained from another apparatus, a condition that a predetermined control signal is received from another apparatus, and a condition that a predetermined operation is made on the second operation unit 25.

The image display process includes, as shown in FIG. 7, an image obtainment step (Step B1) and a display step (Step B2).

[3-2-1. Image Obtainment Step]

The second controller 21 first performs the image obtainment step (Step B1).

In this image obtainment step, the second controller 21 obtains a plurality of frame images F with the accessory information I attached by the image analysis apparatus 1.

In the image obtainment step of one or more embodiments, the second controller 21 receives image data of a plurality of frame images F via the second communication unit 23.

If the image display apparatus 2 includes a reader for a storage medium, the second controller 21 may read image data from a storage medium with the reader.

If the second controller 21 starts the image display process by obtaining a plurality of frame images F as a trigger, this image obtainment step is unneeded.

[3-2-2. Display Step]

After obtaining the plurality of frame images F, the second controller 21 performs the display step (Step B2).

In this display step, the second controller 21 causes the second display 24 to display the frame images F with the accessory information I attached.

In the display step of one or more embodiments, the second controller 21 superimposes, on the (respective) frame images F, the accessory information I indicating the decrease region R in the frame images F.

By this display step, the second display 24 displays the accessory information I superimposed on the (respective) frame images F.

Examples of the superimposition include: overlaying the accessory information I on the decrease region R; and embedding the accessory information I in the decrease region R.

In the attachment control step that is performed by the image analysis apparatus 1, the image analysis apparatus 1 generates one (piece of) accessory information I from the information of the decrease region R, and attaches the accessory information I to frame images F.

Hence, in this display step, the second display 24 displays the one accessory information I generated in the attachment control step superimposed on the frame images F.

Figure 9A:
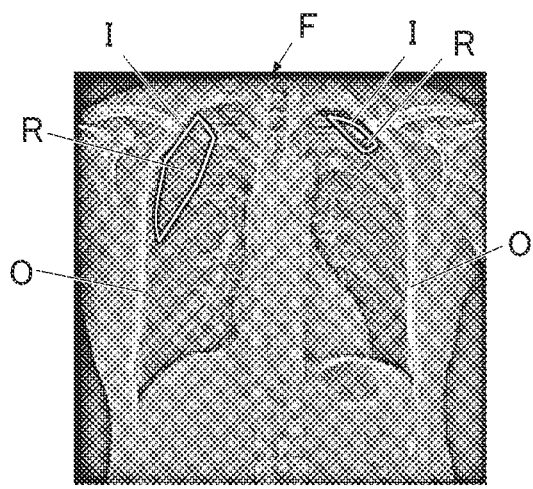
FIG. 9A shows a frame image as an example displayed by the image display apparatus included in the image display system according to one or more embodiments.
Figure 9B:
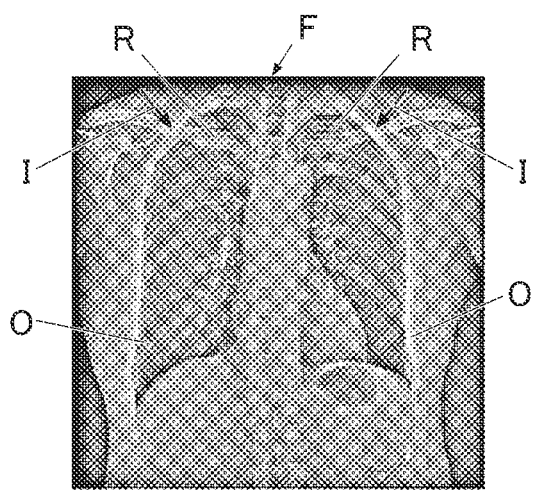
FIG. 9B shows a frame image as another example displayed by the image display apparatus included in the image display system according to one or more embodiments.
Figure 9C:
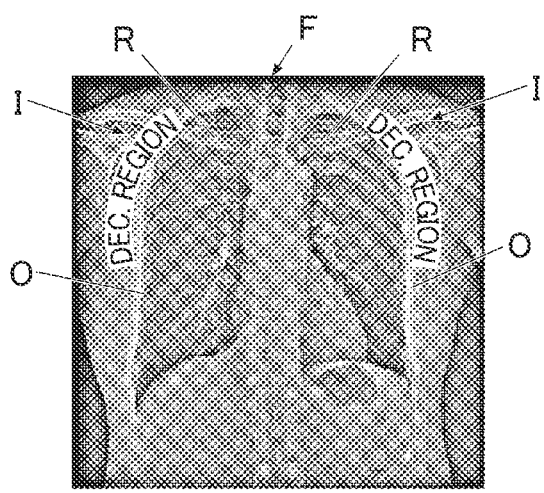
FIG. 9C shows a frame image as another example displayed by the image display apparatus included in the image display system according to one or more embodiments.

In the display step of one or more embodiments, the second display 24 displays the mark generated in the attachment control step superimposed on the frame images F. Examples of the mark include a frame-shaped mark as shown in FIG. 9A, an arrow-shaped mark as shown in FIG. 9B, and character information ("DEC. REGION") as shown in FIG. 9C.

In the attachment control step that is performed by the image analysis apparatus 1, the image analysis apparatus 1 attaches (indicates or shows) the accessory information I to (within or in the vicinity of) the region common (commonly identified region, same position) to (in) the frame images F.

Hence, in this display step, the second display 24 displays, for example, as shown in FIG. 10, the accessory information I superimposed on the region common (commonly identified region, same position) to (in) the frame images F.

As a result, the frame images F displayed by the second display 24 show that the structure O changes its shape with time, whereas the accessory information I is not affected by the temporal change of the structure O and keeps the same shape and size at the same position.

When, in the attachment control step that is performed by the image analysis apparatus 1, the image analysis apparatus 1 attaches the accessory information I to "all" frame images F or "consecutive" frame images F, in this display step, the second display 24 displays the accessory information I indicating the decrease region R in the frame images F showing the dynamic state of the subject superimposed on all of the frame images F or consecutive frame images F of the frame images F (displays an image (dynamic image) in which the accessory information I is superimposed on respective consecutive frame images F).

That is, during the entire period in which the frame images F are being displayed (reproduced), the accessory information I is being displayed. This can prevent the frame images F (accessory information I) from flickering, which is caused by insertion of a frame image(s) F with the accessory information I not attached in the middle of reproduction of the frame images F.

When the image analysis apparatus 1 generates the composite image and attaches the accessory information I to the composite image, in this display step, the second display 24 displays the accessory information I attached to (indicated or shown within or in the vicinity of) the decrease region R of the composite image.

4. Advantageous Effects

As described above, the image analysis apparatus 1 (dynamic image control apparatus) of one or more embodiments includes the first controller 11 (hardware processor) that obtains a plurality of frame images F showing the dynamic state of a subject, identifies, from the obtained plurality of frame images F, a movement decrease region R of a predetermined structure O by user input or detection from the plurality of the frame images F, and performs control to attach accessory information I indicating the identified movement decrease region R to the plurality of frame images F.

Further, as described above, the image display apparatus 2 of one or more embodiments includes: the second controller 21 (hardware processor) that obtains a plurality of frame images F showing the dynamic state of a subject; and the second display 24 (display) that displays accessory information I indicating a movement decrease region R in the obtained plurality of frame images F, the accessory information I being superimposed on consecutive frame images F of the plurality of frame images F.

Hence, according to the image analysis apparatus 1, the image display apparatus 2 or the system 100 including these apparatuses, visibility in interpreting a plurality of frame images F can be improved.

5. Modifications

It is needless to say that the present invention is not limited to the above embodiments or the like, and hence can be appropriately modified within a range not departing from the scope of the present invention.

Figure 11:
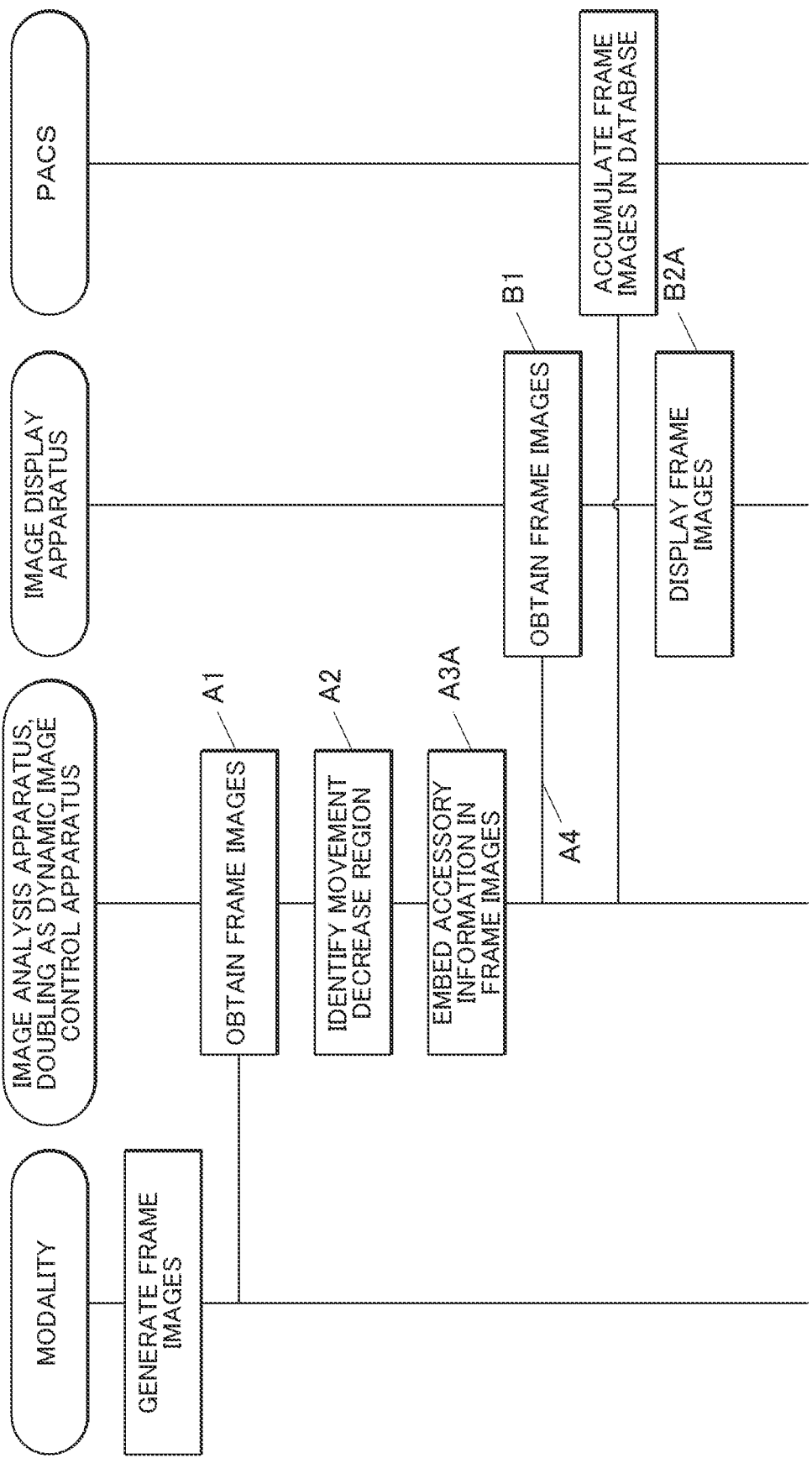
FIG. 11 is a sequence diagram showing another example of the operation of the image display system according to one or more embodiments.

For example, in the system 100, 100B or 100D in which the apparatus that performs the attachment control step (Step A3) and the apparatus that performs the display step (Step B2) are different, for example, as shown in FIG. 11, the apparatus (image analysis apparatus 1, PACS 4A or dynamic image control apparatus 6) that performs the attachment control step (Step A3A) may superimpose (embed) the accessory information I. In this case, the image display apparatus 2 simply obtains the image data of the frame images F with the accessory information I superimposed (embedded) from the apparatus that performs the attachment control step and displays the obtained image data.

Figure 12:
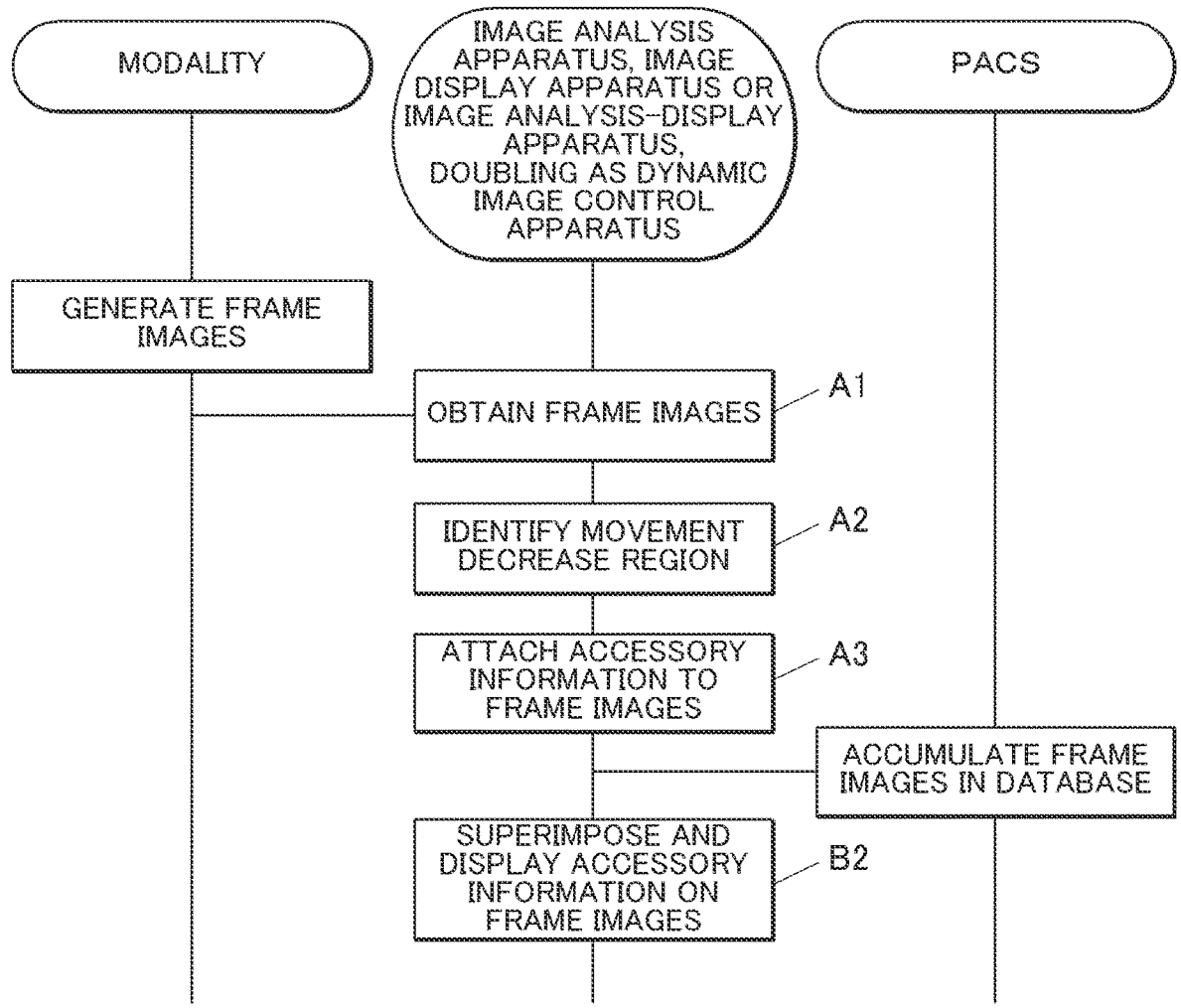
FIG. 12 is a sequence diagram showing another example of the operation of the image display system according to one or more embodiments.

Further, in the system 100, 100A, 100B, 100C or 100D that includes an apparatus including a display, for example, as shown in FIG. 12, the apparatus including the display (image analysis apparatus 1, image display apparatus 2A or image analysis-display apparatus 5) may perform both the dynamic image control process and the image display process. In this case, the output step (Step A4) in the dynamic image control process and the image obtainment step (Step B1) in the image display process are unneeded.

Further, when the PACS 4 or 4A includes a display, in the system 100, 100A, 100B, 100C or 100D, the PACS 4 or 4A may perform the image display process.

Further, in the above, hard disks, nonvolatile semiconductor memories or the like are used as computer readable media of the programs of one or more embodiments of the present disclosure. However, this is not a limitation. As the computer readable media, portable storage media, such as CD-ROMs, can also be used. Further, as media to provide data of the programs of one or more embodiments of the present disclosure via communication lines, carrier waves can be used.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. An image display apparatus comprising:
a hardware processor that obtains frame images showing a dynamic state of a subject; and
a display that displays accessory information indicating a position of a movement decrease region in the subject displayed in the frame images, wherein
the movement decrease region is a region of an organ or tissue of the subject that moves less than a normal movement for that organ or tissue due to adhesion of the organ or tissue, and
the accessory information is superimposed on consecutive frame images of the frame images.

2. The image display apparatus according to claim 1, wherein the display displays the accessory information shown at a same position in the frame images.

3. The image display apparatus according to claim 1, wherein the display displays the accessory information indicating the movement decrease region in a composite image generated from the frame images.

4. The image display apparatus according to claim 1, wherein the movement decrease region is a region common to the frame images without being affected by temporal change of the subject.

5. The image display apparatus according to claim 1, wherein the display displays the accessory information superimposed on all of the frame images.

6. The image display apparatus according to claim 1, wherein
the hardware processor generates, as the accessory information, one piece of accessory information from information of a region that is identified from the frame images and has a movement amount of a predetermined structure,
the movement amount is not greater than or less than a threshold value,
the display displays the one piece of accessory information superimposed on the frame images, and
the threshold value is defined based on the movement amount of a healthy people.

7. The image display apparatus according to claim 1, wherein
the frame images include a start frame image and an end frame image, and
the movement decrease region is a region where a movement vector from the start frame image to the end frame image is not greater than a threshold value for determining presence or absence of adhesion of the organ or tissue.

8. The image display apparatus according to claim 1, wherein
the movement decrease region is a region of a suspected pleural adhesion.

9. An image display apparatus comprising:
a display that displays an image in which accessory information is superimposed on consecutive frame images among frame images showing a dynamic state of a subject, wherein
the movement decrease region is a region of an organ or tissue of the subject that moves less than a normal movement for that organ or tissue due to adhesion of the organ or tissue, and
the accessory information indicates a position of a movement decrease region in the subject displayed in the frame images.

10. The image display apparatus according to claim 9, wherein the display displays the accessory information shown at a same position in the frame images.

11. The image display apparatus according to claim 9, wherein the display displays the accessory information indicating the movement decrease region in a composite image generated from the frame images.

12. The image display apparatus according to claim 9, wherein the movement decrease region is a region common to the frame images without being affected by temporal change of the subject.

13. The image display apparatus according to claim 9, wherein the display displays the accessory information superimposed on all of the frame images.

14. The image display apparatus according to claim 9, wherein
the display displays, as the accessory information, one piece of accessory information generated from information of a region that is identified from the frame images and has a movement amount of a predetermined structure,
the movement amount is not greater than or less than a threshold value,
the one piece of accessory information is superimposed on the frame images, and
the threshold value is defined based on the movement amount of a healthy people.

15. A non-transitory computer readable storage medium storing a control program to cause an image display apparatus that comprises a hardware processor and a display to:
obtain frame images showing a dynamic state of a subject; and
display accessory information indicating a position of a movement decrease region in the subject displayed in the frame images, wherein
the movement decrease region is a region of an organ or tissue of the subject that moves less than a normal movement for that organ or tissue due to adhesion of the organ or tissue, and
the accessory information is superimposed on consecutive frame images of the frame images.

16. An image display system comprising:
an image display apparatus;
a hardware processor that obtains frame images showing a dynamic state of a subject; and
a display that displays accessory information indicating a position of a movement decrease region in the subject displayed in the frame images, wherein
the movement decrease region is a region of an organ or tissue of the subject that moves less than a normal movement for that organ or tissue due to adhesion of the organ or tissue, and
the accessory information is superimposed on consecutive frame images of the frame images.

* * * * *